United States Patent [19]

Mann et al.

[11] 4,260,261

[45] Apr. 7, 1981

[54] OPTICAL FOOD PROBE

[75] Inventors: Walter J. Mann, Little Neck; Aaron A. Rosenblatt, New York, both of N.Y.

[73] Assignee: QED, Chappaqua, N.Y.

[21] Appl. No.: 59,554

[22] Filed: Jul. 23, 1979

[51] Int. Cl.³ .............................................. G01J 3/46
[52] U.S. Cl. ...................................... 356/402; 99/341; 350/96.26
[58] Field of Search ................ 356/402, 241; 73/352; 99/341, 342; 350/96.10, 96.26

[56] References Cited

U.S. PATENT DOCUMENTS

| | | | |
|---|---|---|---|
| 1,783,792 | 12/1930 | Isaacson | 99/341 |
| 3,224,320 | 12/1965 | Knudsen | 356/381 |
| 3,357,433 | 12/1967 | Fourestier et al. | 356/241 X |
| 3,493,774 | 2/1970 | Knudsen | 356/241 X |
| 3,556,085 | 1/1971 | Takahashi | 350/96.26 X |
| 3,724,360 | 4/1973 | Kliewer et al. | 99/342 |
| 3,724,922 | 4/1973 | Jones | 356/241 X |

*Primary Examiner*—F. L. Evans
*Attorney, Agent, or Firm*—Mandeville and Schweitzer

[57] ABSTRACT

The application discloses a food probe comprising an optical rod insertable in a body of food, for example, a roast of meat. At its inner end, the rod is configured to receive and transmit axially through the rod a color image of the food in the area contacted by the end of the rod. The image is transmitted to the outer end, where it is desirably magnified for convenient viewing of internal conditions. If desired, the probe may provide for a plurality of viewing areas, for simultaneously viewing the food at multiple depths. The probe preferably is rigid but may be connected to a flexible fiber optic bundle for viewing at a remote location.

10 Claims, 7 Drawing Figures

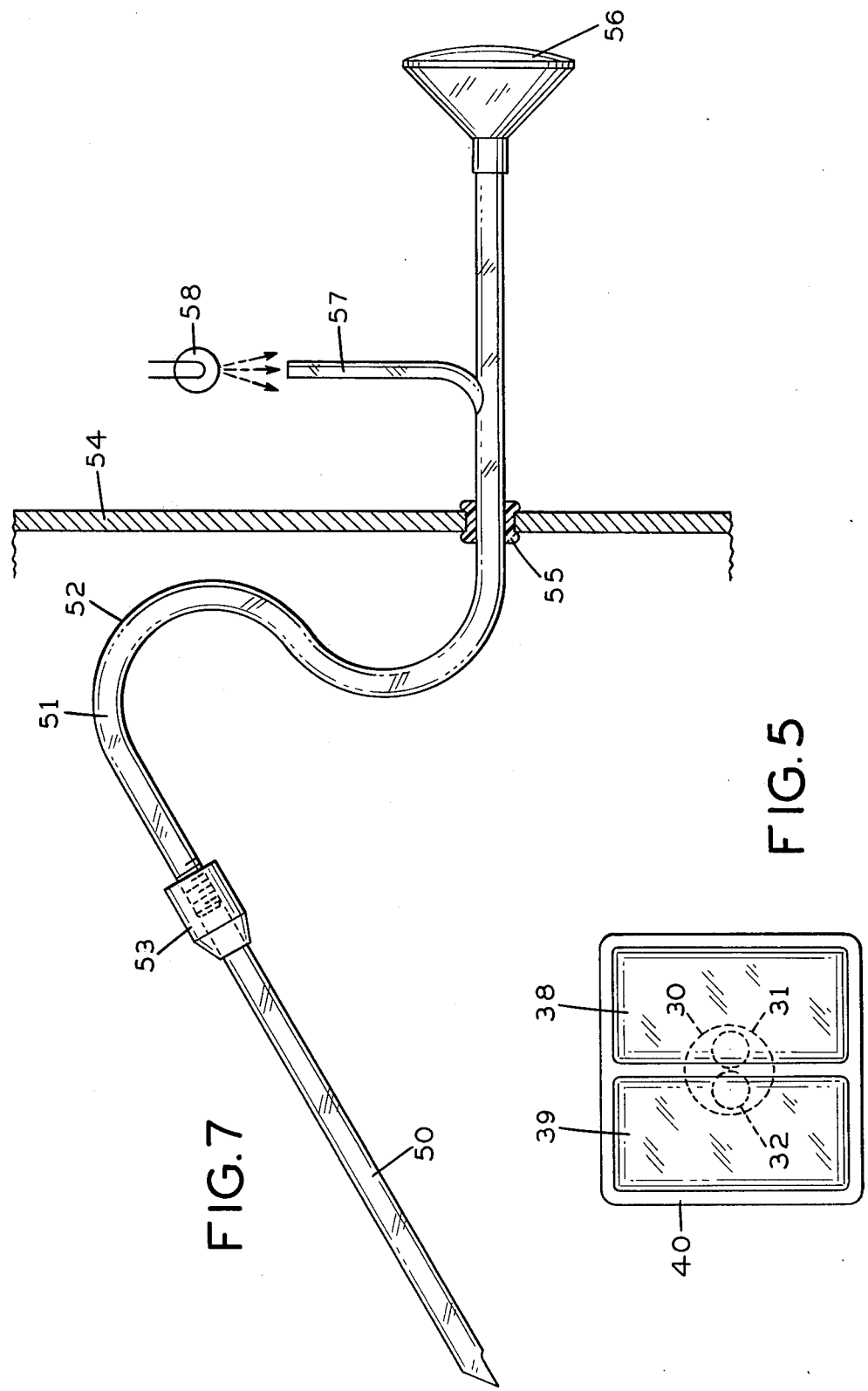

OPTICAL FOOD PROBE

BACKGROUND AND SUMMARY OF THE INVENTION

Determining when food which has been cooking is ready is an inexact science at best. While the outside color of the food may be used as an indicator, it is the color of the inside of the food which is often critical. This is especially true of foods such as roasts where the outside color may not reliably reflect the condition of the inside because of the thickness of the meat. One solution has involved utilization of a probe thermometer to determine the temperature within the food. However, many cooks prefer color as an indicator rather than temperature; for example, often they slice open the meat to ascertain the color therein.

It is an object of the instant invention to provide a way to determine quickly and easily the color of any part of the food. By using the invention, the cook may determine the state of readiness of a roast or steak, at one or more sites or at several depths, upon visual inspection and need not go to the trouble of cutting open the meat.

The device consists of an optical probe which transmits the color of the food. The probe is shaped to pierce the food. Its lower end has a planar surface which enables an image of the food, including its color, to be transmitted to the other end of the probe. The image transmitted may be magnified at the other end so as to facilitate viewing of the color. The probe is placed in the portion of the food that the cook is interested in viewing, and is easily withdrawn when the color has been seen. The probe may be placed at different depths of the food. Thus, if it is desired to inspect the food at additional levels, the probe may be forced deeper into the food. Advantageously, the probe will be made of Pyrex glass so that it will be heat resistant, and it will be tempered, thus ensuring its resistance to breakage.

In one advantageous embodiment, the probe is attached to a fiber optic bundle. The color of the food is thus transmitted from the rod through the fiber optic bundle and into a more convenient viewing area. With this embodiment, the fiber optic bundle may lead to a magnifier on the control panel of an oven, for example, so that the color of the food may be more conveniently viewed from outside the oven.

A further modification of the invention permits the viewing of two or more levels of meat at one time. In that embodiment, two or more rods, and if desired two or more magnifiers, are provided. One of the rods is shorter than the other and its bottom surface is turned sideward so that the surface faces the meat. The viewer may thus observe the meat condition simultaneously at a plurality of depths.

For a more complete understanding of the above and other features and advantages of the invention, reference should be made to the following detailed description of certain preferred embodiments of the invention and to the accompanying drawings.

DESCRIPTION OF THE DRAWINGS

FIG. 5 is a top plan view of the meat probe of FIG. 4.

FIG. 7 is an elevational view, partly in section, of a further modified form of the invention, incorporating an optic fiber bundle for convenient, remote viewing.

DESCRIPTION OF THE PREFERRED EMBODIMENTS OF THE INVENTION

Figure 1:
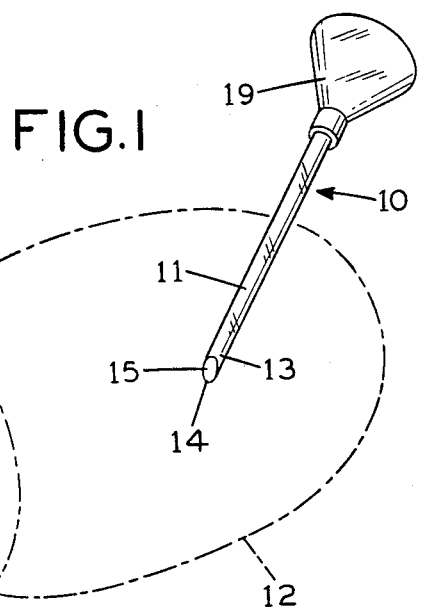
FIG. 1 is a perspective view of a meat probe according to the invention, shown inserted in a meat roast, for example.
Figure 2:
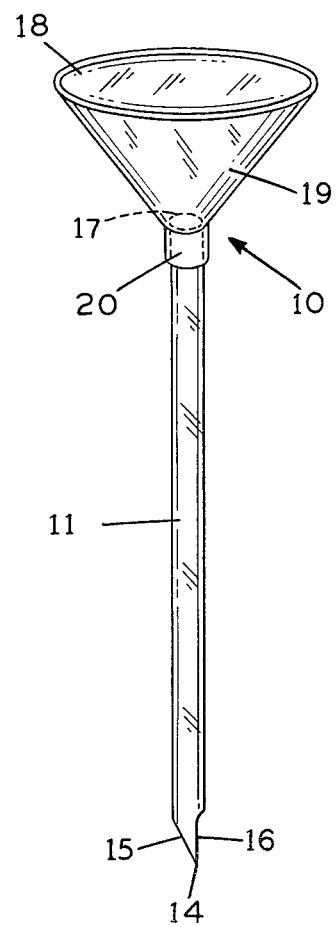
FIG. 2 is an enlarged perspective view of the probe shown in FIG. 1.

Referring to the drawings, and initially to FIGS. 1 and 2 thereof, the probe is generally designated by the reference numeral 10. An optical rod 11 transmits a color image from the meat 12 (see FIG. 1). The rod 11 is formed of heat-tempered glass (Pyrex) or transparent, heat resistant plastic material, suitable to withstand the intended environment, e.g., typical oven temperatures. The rod is constructed to be straight and rigid, and its lower end 13 is shaped to form a piercing edge 14, to enable the rod to be forcibly inserted into the roast.

In the first illustrated form of the invention, the bottom surface 15 of the optical rod (see FIG. 2) is ground flat and at 45 degrees to the axis of the rod. Directly opposite the surface 15, the rod is provided with a flat surface 16 parallel with the rod axis. when the probe is inserted in a roast, the internal color is transmitted laterally through the flat surface 16, reflected off of the angled surface 15, and transmitted axially through the rod 11. The light is transmitted by the rod to its upper end 17 where the color image is magnified by a magnifying lens 18. The lens 18 is held in place by a funnel shaped support 19, which is provided with a sleeve portion 20 bonded to the upper end of the probe rod 11. The lens 19 serves to enhance the light transmitted into the optical rod and also to magnify the image reflected back. However, under some circumstance the invention may be used without benefit of the lens 19, provided the light is adequate to enable the color to be seen at the top of the optical rod.

Most advantageously, the bottom surface 15 of the probe 10 is formed at the described angle to the axis of the rod, because this shape facilitates piercing of the meat. However, other bottom configurations may be utilized, provided a flat viewing surface is presented to the meat and provided further that the proper optical principles are observed, to enable the image to be transmitted up through the rod.

Figure 4:
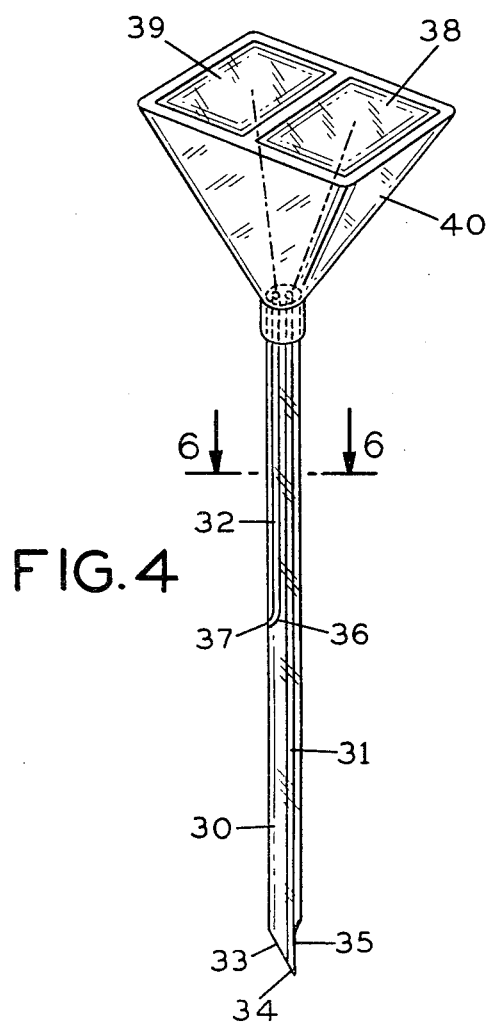
FIG. 4 is a perspective view of a modified form of the invention.
Figure 6:
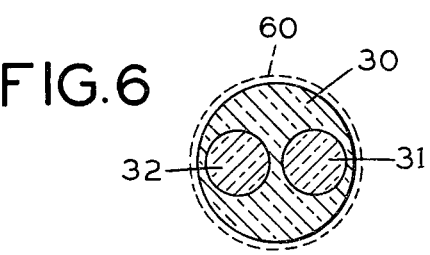
FIG. 6 is an enlarged cross sectional view taken along lines 6—6 of FIG. 4.

A modified form of the invention is depicted in FIGS. 4—6. A rigid, cylindrical matrix rod 30, formed of heat resistant glass or plastic, encapsulates two optical rods 31, 32. The matrix rod 30 is formed at its lower end with a 45 degree angled end surface 33 to facilitate penetration of the rod into the meat. Likewise, the optical rod 31 extends to the lower end of the probe and its extremity 34 is also angled at 45 degrees to be flush with the end of the matrix rod. As in the case of the embodiment of FIG. 1, the side 35 of the optical rod 31 opposite to its beveled surface 34 is ground flat to admit the desired image from the interior of a meat roast. The image is reflected from the surface 34 and transmitted axially up the rod 31.

As shown in FIG. 4, the second optical rod 32 is bent outwardly at its lower end 36, terminating in a flat, planar surface 37 providing visual access to the meat at a level above the end extremity of the probe.

At the upper ends of the optical rods 31, 32 are two magnifying lenses 38, 39 for magnifying the images transmitted to the tops of the rods. The matrix rod 30 is connected at its upper end to a casing 40 which supports the two lenses in properly spaced relation to the rods. As in the previously described embodiment, the lenses enhance the images by magnifying them and also by admitting greater amounts of light. However, since the color images may also be observed by simply looking at the tops of the rods, the lenses and their support means may be omitted in certain cases.

The embodiment of FIGS. 4—6 allows the cook to see two levels of the meat at once. Thus, when the probe is inserted into the meat to the desired level, the color of the meat at the level facing the flat surface 35 of the optical rod 31 can be seen in the magnifying lens 38. Additionally, the color image of the meat at the level opposite the flat lateral surface 37 of rod 36 may be viewed in the lens 39.

Figure 3:
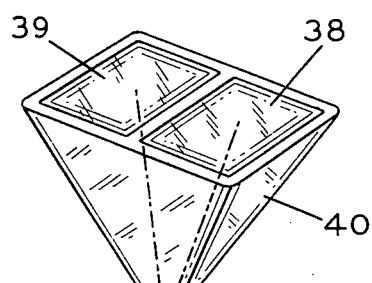
FIG. 3 is a top plan view of the probe.

A still further modification of the invention is shown in FIG. 7. There, the same type of optical rod 50 may be utilized as in the embodiment of FIGS. 1-3. However, instead of directly magnifying the color image at the top of the optical rod, the image is further transmitted through a fiber optic bundle 51. Advantageously, the fiber optic bundle 51 is covered with a temperature resistant flexible polymer 52 and is attached to the optical rod 50 through a coupler 53. The optic fiber bundle 51 may, for instance, lead through the oven wall 54, through a suitable grommet 55, to a magnifying lens 56. The magnifying lens is advantageously located on the oven control panel, for example.

A portion 57 of the optical fiber, for example, one-third, may be diverted to a light source 58. The advantages of this embodiment are manifest. The fiber optic bundle permits particularly easy viewing of the color of the meat in that the rod is simply inserted in any part of the meat and the cook is able to observe the condition of the meat, as cooking progresses, by glancing at the oven panel to ascertain the internal color of the meat. Diversion of a portion of the optical fibers to an independent light source provides an especially effective illumination of the interior of the meat.

Although the glass material forming the probe is considered amply strong for the purpose, it may be desirable to encase the rod in a surrounding metal tube, as for example is reflected in broken lines in FIG. 6, designated by the reference numeral 60. Similarly, it may be desirable in cases to provide a vacuum metallized or similar coating of the surface of the glass probe to improve the optical transmission characteristics. Such a coating could be in addition to the casing 60, if desired.

Particularly in cases where it is desirable to utilize a fiber optic bundle for remote viewing, it may be appropriate to provide for the probe itself to be formed of an end section of the fiber optic bundle. To this end, a suitable length of the fiber bundle is encased in a rigid tube or matrix to provide adequate rigidity for insertion of the probe into the food. It would also be possible, of course, to utilize a rigidly encased fiber optic bundle to form the probe portion in the form of the invention illustrated in FIGS. 2 and 4, for example.

It will be understood that, when using an encased fiber optic bundle to form the probe section, each of the individual optical fibers forms a separate viewing surface at its end, and the configuration of the lower end of the probe becomes relatively unimportant from an optical standpoint.

It should be understood, of course, that the illustrated forms of the invention are intended to be representative only, as certain changes may be made therein without departing from the clear teachings of the disclosure. Accordingly, reference should be made to the following appended claims in determining the full scope of the invention.

We claim:

1. An image transmitting food probe or the like for determining the state of readiness of food, comprising
   (a) an optical rod having an upper end and a a lower end,
   (b) said upper end having a receiving surface such that an image transmitted through the rod from the lower portions thereof will be visible at said receiving surface,
   (c) said lower end having a penetrating portion and a planar image-receiving surface for transmission of color into the rod.

2. A food probe or the like according to claim 1, further characterized by
   (a) said penetrating portion comprising a flat surface disposed at 45 degrees to the axis of said rod, and
   (b) said image-receiving surface being disposed parallel to said axis and opposite the angularly disposed flat surface.

3. A food probe or the like according to claim 1, further characterized by
   (a) said probe including a second optical rod generally parallel to the first,
   (b) rod-like support means surrounding said optical rods,
   (c) said support means having an angularly disposed lower end exposing portions of said first mentioned optical rod, and
   (d) said second optical rod having a flat surface portion exposed along the side of said support means, at a level above the lower end thereof.

4. A food probe or the like according to claim 1, further characterized by
   (a) a metallic tube surrounding and supporting said optical rod.

5. A food probe or the like according to claim 1, further characterized by
   (a) optical magnification means mounted adjacent the upper end of said optical rod.

6. A food probe or the like according to claim 3, further characterized by
   (a) optical magnification means mounted adjacent the upper end of said rod-like support and including separate image forming means associated with each of said optical rods.

7. A color transmitting food probe, comprising
   (a) an optical rod made of heat resistant, tempered glass having a lower end and an upper end,
   (b) said lower end having piercing means suitable for piercing the food whose color is to be viewed,
   (c) said lower end having a generally planar surface for transmission of the color of the meat,
   (d) a flexible fiber optic bundle made of heat resistant, tempered glass for transmission of the color of the food,
   (e) said fiber optic bundle being joined to the upper end of said optical rod, and
   (f) viewing means associated with the fiber optic bundle and positioned so as to display the image of the food conveyed through the optical rod and the fiber optic bundle.

8. A color transmitting food probe according to claim 7, further characterized by
   (a) a light source,
   (b) a portion of the optical fibers within said fiber optic bundle being directed to said light source for illumination of the rod.

9. A color probe, comprising
   (a) a color transmitting instrument having an attachment end and a piercing end,
   (b) said piercing end having piercing means so as to pierce the object to be viewed and being suitable for transmitting internal color of the object,
   (c) said color transmitting instrument having an optical rod for transmitting the color from the piercing end to the attachment end,
   (d) a fiber optic bundle suitable for transmission of the color transmitted by the color transmitting instrument,
   (e) said fiber optic bundle being coupled with said color transmitting instrument so that the bundle transmits the color image transmitted by said instrument, and
   (f) a magnifying lens positioned so as to magnify the image transmitted by said instrument.

10. A device for determining the color inside of food to ascertain the state of preparation thereof, which comprises
    (a) a food color transmitting probe having a viewing end and a piercing end,
    (b) said piercing end having an image receiving surface at its piercing end,
    (c) said piercing end being sharp enough for plunging the probe into the food to be tested.
    (d) said probe being operative to transmit the color image from the piercing end to the viewing end.

* * * * *